United States Patent [19]

Ungerstedt

[11] Patent Number: 4,694,832
[45] Date of Patent: Sep. 22, 1987

[54] DIALYSIS PROBE

[76] Inventor: Carl U. Ungerstedt, Mjölnarstigen 11, S-18146 Lidingö, Sweden

[21] Appl. No.: 800,374

[22] Filed: Nov. 22, 1985

Related U.S. Application Data

[63] Continuation of Ser. No. 554,116, Nov. 21, 1983, abandoned.

[30] Foreign Application Priority Data

Dec. 1, 1982 [SE] Sweden .............................. 8206863

[51] Int. Cl.⁴ .............................................. A61B 5/00
[52] U.S. Cl. .................................... 128/632; 128/760
[58] Field of Search .................. 128/632 E, 760, 769; 73/863.23

[56] References Cited

U.S. PATENT DOCUMENTS

| | | |
|---|---|---|
| 3,483,990 | 12/1969 | Litle et al. . |
| 3,494,470 | 2/1970 | Banfield . |
| 3,572,315 | 3/1971 | Cullen .................... 128/632 |
| 3,640,269 | 2/1972 | Delgado . |
| 3,658,053 | 4/1972 | Fergusson et al. .................... 128/632 |
| 3,830,106 | 8/1974 | Gardiner et al. . |
| 4,016,863 | 4/1977 | Brantigan .................... 128/632 |
| 4,016,864 | 4/1977 | Sielaff et al. . |
| 4,221,567 | 9/1980 | Clark et al. . |
| 4,235,231 | 11/1980 | Schindler et al. . |
| 4,274,417 | 6/1981 | Delpy .................... 128/632 |
| 4,340,615 | 7/1982 | Goodwin et al. .............. 128/632 X |

FOREIGN PATENT DOCUMENTS

| | | |
|---|---|---|
| 2344013 | 3/1977 | France . |
| 2474317 | 1/1980 | France . |
| 2053719 | 5/1980 | United Kingdom . |

OTHER PUBLICATIONS

Ungerstedt et al., "Dopamine Synaptic Mechanisms Reflected in Studies Combining Behavioural Recordings and Brain Dialysis", *Advances in the Biosciences*, vol. 37, (1982) pp. 219–231.

Delgado et al., "Dialytrode for Long Term Intracerebral Perfusion in Awake Monkeys", *Arch. Int. de Pharmaco. et de Therapie*, vol. 198, No. 1, Jul. 1972, pp. 9–21.

Primary Examiner—Edward M. Coven
Attorney, Agent, or Firm—Young & Thompson

[57] ABSTRACT

A dialysis probe, primarily intended for insertion in biological tissues, for example brain tissue, comprises a dialysis membrane and ducts for flow of the perfusion fluid over the membrane. The dialysis membrane in such a probe can be surrounded by a mounting which supports and partially reveals the membrane, and which is more rigid than the membrane.

1 Claim, 6 Drawing Figures

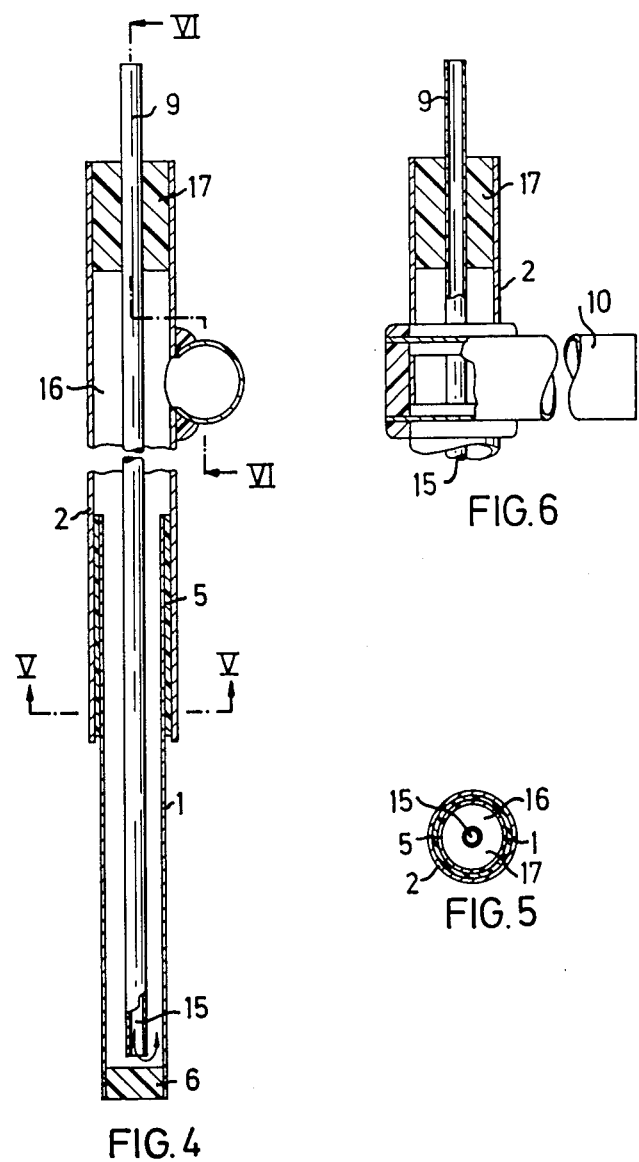

DIALYSIS PROBE

This application is a continuation of application Ser. No. 554,116, filed 11/01/83, abandoned.

Biological tissues consist of cells which live in a fluid environment which transports nutrients and decomposition products to and from the cells and adjacent blood vessels. Through this extracellular fluid space, all the building blocks necessary for the metabolism of the individual cell are transported but also all the signal substances which notify the cell of the body's requirements. Examples of such signal substances are hormones such as insulin, estrogen and others. An especially important form of transport occurs in the nervous system; the electrical nerve impulses release signal substances (transmitters) which flow from the end of one nerve cell to the receiving molecules, the receptors, of the other nerve cell. The functioning of the brain is as a whole a result of the release of these transmitters. Diseases of the brain are therefore assumed to be dependent on disturbances in the release of transmitters and the pharmaceuticals with which brain-diseased patients are treated are known to affect these substances.

In order to understand the functioning of the body, it is particularly important to be able to follow the "traffic" of substances between the cells of the body and between the cells and the blood vessels. Traditionally, this has been done either by extracting blood for analysis of its contents or by perfusion of blood vessels with a physiological fluid the contents of which can then be studied. These methods provide, however, only an indirect indication of the intercellular environment and are also difficult to apply to many organs. This especially applies to the brain where it is impossible to perfuse the blood vessels which go to certain defined regions. Therefore attempts have been made to develop new techniques, e.g. the so-called push-pull technique in which two tubes are inserted into the brain and fluid is pressed through one at the same time as the same amount is drawn out through the other (GADDUM J. H. (1961), J. Physiol., 155, 1-2). In this manner a small cavity is flushed which is created at the ends of the tubes and chemical substances from adjacent cells are extracted with the fluid, which can then be analyzed with regard to its contents. The problems involved in injecting and extracting fluid in a reproducible manner without at the same time creating the risk of damage to surrounding tissue are apparent. In research, this technique has also been difficult to apply to small test animals.

Another known manner of carrying out a sampling of the content of the extracellular space is to apply the dialysis principle. In tissue dialysis, a dialysis probe, comprising a dialysis membrane and ducts for the flow of perfusion fluid over the membrane, is inserted into the tissue and perfusion fluid then flows over the membrane and is then collected and chemically analyzed. Such tissue dialysis can be carried out in essentially all tissues. The dialysis is performed in a defined region, produces very little trauma, is methodologically simple to carry out and is particularly suited to studies of the functioning of the brain. Known dialysis probes for this purpose comprise either two ducts running side by side in the form of a push-pull cannula, the distal end of which terminates in a small sack of permeable material, which sack is then the dialysis membrane (DELGADO, J. M. R. et al. (1972), Arch. int. de Pharmacod. et de Therapie, 198, 1, 9-21), or the ducts for the perfusion fluid are in the form of two sequentially placed duct portions which are joined to each other by means of a membrane which is also in the form of a hose, and which thus joins the two duct forming hose portions and may be curved in the form of a horse shoe (Ungerstedt, U. et al. (1982), Advances in the Biosciences, 37, 219-231, Oxford and New York: Kohsaka, M. et al. (Ed.)).

Both of these known dialysis probes have however, significant deficiencies. In addition to being difficult to put in place, the membranes have the disadvantage of being insufficiently defined as regards the effective dialysis surface area and properties. It is also difficult to assure the correct fluid flow past the membrane. In the sack-shaped membrane, there is the latent risk that one or the other of the duct openings inside the membrane will be blocked by the membrane's own flexible wall material. A tubular membrane, which can be a hollow fibre, can be easily deformed and the flow duct shut off as soon as the membrane is bent, and therefore a microsuture should be placed in the membrane to keep it open. Furthermore, in order to put a probe with a tubular membrane in place, some type of additional supporting means is required inside the membrane as it is being put in place. This supporting means must then be removed before the probe is used.

Provided that a suitable dialysis probe can be produced which is free of the disadvantages mentioned here in known probes, the dialysis technique as such should have significant clinical use, such as in monitoring the status of the brain after skull trauma, e.g. by determining the various metabolic products or transmitters and by measuring oxygen and glucose metabolism. With the aid of suitable isotopes, different aspects of brain function can be followed as well. Metabolic studies of tumours can be carried out on which to base diagnosis. In cytotoxin treatment, dialysis can also be used as a monitor of the amount of cytotoxin reaching the tumour or the amount which normal tissue is subjected to. It should also be possible to administer cytotoxins locally by reverse dialysis whereby the cytotoxins leave the dialysis fluid and penetrate into the tissue to be treated. In clinical as well as research contexts, the penetration of a pharmaceutical into the brain or other tissues can be studied with this dialysis method. Dialysis can of course also be used in other organs than the brain, i.e. in liver function studies, in studies of muscle metabolism, heart metabolism e.g. during and after surgery, in puncture of tumours for diagnosis and treatment and in a number of intensive care situations where the fluid status and metabolism can be followed subcutaneously or in the organs or cavities of the body. A suitable dialysis probe should also be able to be inserted into blood vessels for continuous monitoring of blood status without the need for blood samples from the patient. The probe may also be used in various in vitro situations such as sampling of metabolic products in various cell cultures, fermentation vessels etc. The dialysis can then either be transferred to a chemical laboratory for analysis or in suitable cases be directly connected to a suitable measuring apparatus.

The present invention relates to a dialysis probe of the known type described here and which comprises a dialysis membrane and ducts for the flow of perfusion fluid over the membrane.

The purpose of the invention is, starting from such a probe, to suggest a new and improved probe which is primarily intended for insertion in biological tissue and does not have the disadvantages discussed above. Furthermore, the new and improved probe, without being limited in its use to only biological tissues, must make possible the routine use of tissue dialysis technique in both clinical and preclinical research. Different embodiments must be usable in humans or larger test animals and in small test animals in various fields of research.

A dialysis probe made according to the invention which in tests in the tissues of small test animals proved to fulfil this purpose, is primarily characterized in that its dialysis membrane is surrounded by a mounting which supports and partially reveals the membrane, and is more rigid than the membrane. By virtue of the fact that the mounting of the membrane in a dialysis probe made according to the invention is more rigid than the membrane itself and thereby supports and protects the membrane, and furthermore only reveals part of the membrane so that the size and shape of the portion(s) of the membrane taking part in dialysis can be adapted to the size and shape of the tissue location to be studied, a probe according to the invention will be both robust and quite easy to handle as well as being easily inserted for use. As a result of the well-defined shape and size of the membrane portion taking part in dialysis, it can be used with directed effect.

Probes made according to the invention can have many varying shapes, from more or less spherical to elongated shapes. In an embodiment especially useful for dialysis of brain tissue, and which can be varied in many ways and is at the same time relatively simple and inexpensive to manufacture, the dialysis membrane and the mounting are essentially tubular with the membrane at least partially inserted in the mounting. This construction, which provides the probe with an elongated and relatively easily appliable external shape, allows the dialysis membrane to either have its distal end freely exposed and projecting out of the mounting or it can be completely contained therein. In the first case, the revealed portion participating in dialysis is at the distal end of the probe, while the corresponding membrane in the latter case, is exposed by one or more openings in the wall of the mounting. In both cases, the distal ends of both the dialysis membrane and the mounting are sealed. In the latter case, the sealing of these ends can be common to both the dialysis membrane and the mounting.

To not do undue damage to tissue, the distal end of the probe can be suitably rounded. In some cases, it can be advantageous however to make the distal end of the probe pointed to facilitate placement in the place of use. For the same reasons, said end can also be provided with a possibly pointed, cutting edge. With such an edge, a probe according to the invention can be inserted in a blood vessel or in tissue in the same manner as a cannula.

In an especially advantageous embodiment of a dialysis probe according to the invention, the ducts for flow of the perfusion fluid over the membrane are accessible from the outside at the proximal end of the probe. They can be arranged to protrude from said end and are possibly surrounded by an extra protective casing. Significant advantages are won if the ducts accessible at said probe end have means for connection to the required apparatus for the dialysis process which can be of any different types and are not encompassed by the present invention. The connection between this apparatus and a probe according to the invention preferably consists of hoses with one or more ducts of suitable dimensions. The connecting means at the proximal end of the probe can either extend from the probe axially to the probe or at least one of the connecting means can extend more or less radially from the probe. The latter is especially advantageous for probes to be used on small test animals.

To assure the best possible perfusion fluid flow over the portion of the membrane participating in dialysis in a probe made according to the invention, one of the fluid channels has its opening inside the probe located in the vicinity of the distal end of the portion of the membrane exposed by the mounting, while a second duct has its opening inside the probe located in the vicinity of the proximal end of this membrane portion. A particularly simple embodiment is obtained if the duct located in the vicinity of the proximal end of the exposed membrane portion consists of an open space inside the probe, in which space the duct extends which has its opening in the vicinity of the distal end of said membrane portion. Thus only one duct element will be used, while the other duct is formed by an open space within the probe surrounded by the membrane mounting. It is suitable that this duct-forming open space inside the probe communicates with a connecting means extending laterally from the probe, in the form of a pipe socket or the like.

The invention will be described below in more detail with reference to two embodiments shown in the accompanying drawings for dialysis probes made according to the invention.

FIG. 4 shows an axial section corresponding to FIG. 1 through a probe variant according to the invention primarily intended for use on experimental animals.

FIGS. 5 and 6 show sections along the lines V—V and VI—VI through said variation.

For the sake of clarity, all of the drawings are drawn on an enlarged scale. A dialysis probe made according to the invention can have very small dimensions, for example only fractions of a millimeter in the case of brain tissue dialysis.

As can be seen from the preceding, and as the drawings show, a dialysis probe made according to the invention comprises a dialysis membrane with associated ducts for achieving a perfusion fluid flow over the membrane. This can in principle be made in any suitable manner and the number and shape of the ducts can also vary. The only crucial factor is that the required perfusion fluid flow must be maintained over the portion or portions of the membrane participating in dialysis.

In the two embodiments shown here for a probe according to the invention, the dialysis membrane 1 is essentially tubular, which has proved to be advantageous both as regards function and manufacture. According to the invention, the membrane is surrounded by a mounting 2 which supports and partially exposes the membrane, and which is more rigid than the membrane 1. In addition to providing support to the membrane 1, the mounting thus also protects the membrane, whereby a probe according to the invention is quite handlable, which is an advantage both in manufacture as well as in storage and use of the probe. In the two embodiments shown, the mounting 2 is essentially tubular and consists of a thin-walled metal sleeve of such shape and inner-diameter that the tubular dialysis membrane 1 can be inserted in the same. In order to have the required dialysis properties, the membrane 1 itself consists of a thin-walled suitable permeable hose material. The construction takes advantage of the easily available "hollow fibre" membranes that may be obtained in various sizes and with various dialytic properties to suit the particular application of tissue dialysis. The membranes can then be easily inserted into the outer supporting tube.

Figure 1:
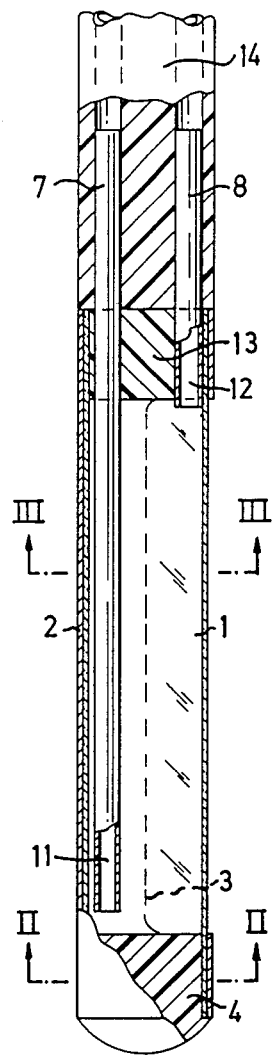
FIG. 1 shows an axial section through a probe primarily intended for use on humans.
Figure 3:
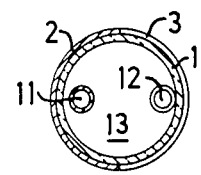
FIGS. 2 and 3 show cross sections through the same along the lines II—II and III—III, respectively in FIG. 1.
Figure 2:
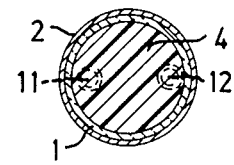

In the probe embodiment shown in FIGS. 1–3, which is primarily intended for use on humans, the dialysis membrane 1 is inserted in its entirety in the mounting 2 consisting of a metal sleeve, the wall of which has an opening 3 in which a portion of the membrane surface is exposed. The size and shape of the opening 3 can be varied depending on the desired size and shape of the dialyzing surface of the membrane. The membrane 1 is inserted in the mounting to be as close as possible to the wall of the mounting. The distal ends of both the dialysis membrane and the mounting are sealed together by epoxy resin 4, for example, in such a manner that the tubular membrane is also sealed against the mounting. The sealing of the distal end of the probe is suitably adapted to the shape of the mounting and can be varied in shape from abruptly cut off to sharpened like an injection cannula. In the probe shown in FIG. 1, the seal is rounded in shape to avoid undue damage to tissue.

In the probe embodiment shown in FIGS. 4–6, which is primarily intended for use on experimental animals, the tubular dialysis membrane 1 is only partially inserted in the mounting 2 consisting of a metal sleeve which is also tubular, so that the distal end of the membrane projects freely from the mounting. In order to be firmly fixed and carefully sealed in relation to the mounting, the proximal end of the membrane is glued with epoxy resin 5, for example, in the mounting. The distal end of the membrane is squarely cut off and sealed by means of a plug 6 of epoxy resin, for example.

In most embodiments of a diffusion probe according to the invention, the ducts for perfusion fluid flow over the membrane 1 should be accessible from the outside at the proximal end of the probe. In the two embodiments shown here, there are means for connecting the perfusion fluid ducts to the rest of the dialysis apparatus at the proximal ends. These means consist of projecting tubular connecting pieces 7, 8 and 9, 10. In the embodiment shown in FIG. 1, these pieces which are direct continuations of the ducts extending inside the membrane, extend out from the probe axially thereof. In the embodiment shown in FIG. 4, only one connecting piece 9 extends axially out from the probe, while the other one 10 extends radially. This arrangement with the perfusion fluid ducts connecting pieces pointing in different directions has significant practical advantages in connection with experimental animals.

As can be seen from the above, the connecting pieces 7–10 projecting from a probe according to the invention are to be regarded as projecting parts of the ducts required for achieving the perfusion fluid flow past the dialyzing surface of the membrane 1. In the embodiment shown in FIG. 1, there are two ducts 11, 12 for the perfusion fluid flow. Both have the shape of thin-walled metal tubes, which project through a seal 13 made of epoxy resin for example, sealing the proximal ends of both the membrane 1 and the mounting 2. It is the projecting ends of these two metal tubes which form the connecting pieces 7,8, on which a two-duct catheter 14 is slipped to connect the probe to the rest of the dialysis apparatus. The two metal tubes or ducts 11,12 have a diameter so that they fit inside the probe, one duct 11 having its opening located in the vicinity of the distal end of the portion of the membrane 1 exposed by the mounting, while the other duct 12 has its opening inside the probe located in the vicinity of the proximal end of said membrane portion. The longer of the two ducts 11,12 is intended for introduction of the perfusion fluid, while the shorter duct is intended for drawing off the fluid.

A probe of the type shown in FIG. 1 can be inserted in a biological tissue through an insertion tube of vein cannula type in which the inner cannula is removed and is replaced with the probe, which is then suitably connected to a flexible hose 14 to adapt to the movements of the tissue in question.

In the embodiment shown in FIG. 4, there are also two ducts 15,16 for the circulation of the perfusion fluid through the probe. Here the duct 16 with its opening located in the vicinity of the proximal end of the exposed membrane portion consists of an open annular space inside the probe. This space surrounds the duct 15 with its opening in the vicinity of the distal end of the membrane and is in open communication with the tube piece 10 extending laterally from the probe, while the other duct 15, which suitably consists of a metal tube, projects out of the probe with an end which forms the axial connecting piece 9 of the probe. Suitably, the proximal end of the probe is sealed with an epoxy resin plug 17 for example, in which the fluid duct 15 consisting of a metal tube is fixed.

The longer of the two ducts 15, 16 leads the perfusion fluid to the distal end of the probe, where the duct 15 opens. The fluid then flows up between the wall of the membrane 1 and the outside of the duct 15, and the actual dialysis takes place. Closer to the proximal end of the probe, the fluid rises up through the annular duct 16 to finally be drawn off through the connecting piece 10 projecting radially from the probe. The size of the dialyzing surface can be varied in this type of probe according to the invention by adapting the portion of the membrane 1 exposed outside the mounting 2.

As is apparent both from FIG. 1 and from FIG. 4, the outer exposed surface of the membrane 1 is free to contact biological tissue into which the probe is inserted. The duct 11 of FIG. 1 and 15 of FIG. 4 extends to the distal end of the hollow fiber membrane and is open to the distal end of the membrane and has an external diameter substantially less than the internal diameter of the membrane. Substantially all of the inner surface of the membrane opposite the outer exposed surface of the membrane is exposed to the flow of liquid between the ducts 11 and 12 of FIG. 1, and 10 and 15 of FIG. 4.

This probe, which is primarily intended to be inserted in the brain of an experimental animal, is inserted through a hole made in the skull. The probe is fixed to the surface of the skull with a suitable adhesive agent such as dental cement.

The invention is not limited to the two embodiments described here and shown in the drawings, but can be modified in many ways within the scope of the patent claims.

What I claim is:

1. A dialysis probe for insertion into biological tissues, comprising a hollow fibre dialysis membrane of uniform cross-sectional configuration throughout its length, an elongated mounting that surrounds and supports and includes means for partially exposing the outer surface of the membrane so that the outer exposed surface of the membrane is free to contact biological tissue in which the probe is inserted, the mounting having an exposed outer surface and being substantially more rigid than the membrane and having an internal diameter greater than the greatest external diameter of the membrane, and ducts for supplying and removing perfusion liquid to and from the interior of the membrane, one of said ducts extending to the distal end of the hollow fibre membrane and being open to the distal end of the membrane, said one duct being disposed inside the hollow fibre membrane and having an external diameter substantially less than the internal diameter of the hollow fibre membrane, the other duct communicating with the proximal end of the hollow fibre membrane, substantially all the inner surface of the membrane opposite said outer exposed surface of the membrane being exposed to the flow of liquid between said ducts.

* * * * *